(12) United States Patent
Sundar et al.

(10) Patent No.: US 8,147,448 B2
(45) Date of Patent: Apr. 3, 2012

(54) HIGH PRECISION INFUSION PUMPS

(76) Inventors: Satish Sundar, San Jose, CA (US);
Swaminathan Balakrishnan, Flower Mound, TX (US); Ivan Melnyk, Coquitlam (CA)

( * ) Notice: Subject to any disclaimer, the term of this patent is extended or adjusted under 35 U.S.C. 154(b) by 0 days.

(21) Appl. No.: 12/678,426

(22) PCT Filed: Sep. 17, 2008

(86) PCT No.: PCT/US2008/706729
§ 371 (c)(1),
(2), (4) Date: Mar. 16, 2010

(87) PCT Pub. No.: WO2009/039214
PCT Pub. Date: Mar. 26, 2009

(65) Prior Publication Data
US 2010/0211003 A1    Aug. 19, 2010

Related U.S. Application Data

(60) Provisional application No. 60/994,194, filed on Sep. 17, 2007, provisional application No. 61/003,384, filed on Nov. 17, 2007.

(51) Int. Cl.
*A61M 5/168* (2006.01)
*A61M 5/145* (2006.01)

(52) U.S. Cl. ............................ 604/67; 604/131; 604/151

(58) Field of Classification Search .................... 604/63, 604/65, 67, 131, 134–136, 151
See application file for complete search history.

(56) References Cited

U.S. PATENT DOCUMENTS

| | | | |
|---|---|---|---|
| 4,038,982 A | 8/1977 | Burke | |
| 4,328,801 A | 5/1982 | Marx | |
| 4,437,337 A * | 3/1984 | Fenrick | ........................ 73/54.01 |
| 4,525,163 A | 6/1985 | Slavik | |
| 4,690,673 A | 9/1987 | Bloomquist | |
| 4,857,048 A | 8/1989 | Simons | |
| 4,952,205 A * | 8/1990 | Mauerer et al. | .................. 604/67 |
| 5,186,057 A | 2/1993 | Everhart | |
| 5,472,420 A | 12/1995 | Campbell | |
| 5,533,981 A * | 7/1996 | Mandro et al. | ................. 604/208 |
| RE35,979 E * | 12/1998 | Reilly et al. | ................... 600/432 |
| 6,063,052 A | 5/2000 | Uber | |
| 6,592,551 B1 * | 7/2003 | Cobb | ............................. 604/155 |
| 6,669,909 B2 | 12/2003 | Shvets | |
| 7,025,226 B2 | 4/2006 | Ramey | |
| 2001/0056259 A1 * | 12/2001 | Skinkle et al. | ................ 604/151 |
| 2002/0045854 A1 | 4/2002 | Royo | |
| 2002/0123716 A1 * | 9/2002 | VanDiver et al. | ................ 604/65 |
| 2006/0142692 A1 | 6/2006 | Jacobson | |
| 2007/0093752 A1 | 4/2007 | Zhao | |

FOREIGN PATENT DOCUMENTS

WO  PCT/US2005/010010    10/2005

* cited by examiner

*Primary Examiner* — Quynh-Nhu H Vu
(74) *Attorney, Agent, or Firm* — Mark Wisnosky

(57) ABSTRACT

A system architecture for closed loop control of infusion devices is described. The architecture provides means to control the flow from an infusion device as well as in some embodiments the pressure of the delivery. A variety of infusion systems are described that use the closed loop control architecture. In some embodiments the closed loop control may be adapted to current commonly used infusion means such as a gravity feed intravenous system. Other embodiments describe infusion pump system that use biasing or drive mechanisms of springs, elastomers, rotary and linear motors.

6 Claims, 12 Drawing Sheets

HIGH PRECISION INFUSION PUMPS

CROSS-REFERENCE TO RELATED APPLICATIONS

This application claims the benefit of: U.S. Provisional Patent Application 60/994,194, filed Sep. 17, 2007, entitled, "More Apparatuses for Low Cost Infusion Pumps, currently pending, by the same inventors, incorporated by reference, and, U.S. Provisional Patent Application 61/003,384, filed Nov. 17, 2007 entitled "Cost-Effective, High Precision Infusion Pumps" currently pending, by the same inventors and incorporated by reference.

TECHNICAL FIELD

This invention presents apparatuses for infusion pumps, infusion pump controllers, and describes the methods for their control.

BACKGROUND

An infusion pump infuses fluids, medication or nutrients into the circulatory system of the patient being treated. Infusion pumps are used to administer fluids in ways that would be impractically expensive or unreliable if performed manually by nursing staff. Commercial infusion pumps can administer injections as small as tens of nanoliters in a single injection and typically can deliver less than 100 microliters per hour on a continuous basis. These delivery volumes levels are too small for a drip and the delivery rate and timing are not practical for manual injections. Infusion pumps can deliver injections on a scheduled time interval, for example every minute, and can deliver injections with repeated boluses requested by the patient, up to pre-selected maximum number per hour (e.g. in patient-controlled analgesia). Infusion pumps can also be programmed to deliver fluids whose volumes vary by the time of day.

Because they can also produce quite high pressures, infusion pumps can also inject controlled amounts of fluids subcutaneously (beneath the skin), or epidurally (just within the surface of the central nervous system—a very popular local spinal anesthesia for childbirth). Different types of infusion include—but are not limited to:

Continuous infusion usually consists of small pulses of infusion, usually between 20 nanoliters and 100 microliters, depending on the pump's design, with the rate of these pulses depending on the programmed infusion speed.

Intermittent infusion has a "high" infusion rate, alternating with a low programmable infusion rate to keep the cannula open. The timings are programmable. This mode is often used to administer antibiotics, or other drugs that can irritate a blood vessel.

Patient-controlled Analgesia is infusion on-demand, usually with a preprogrammed ceiling to avoid intoxication. The rate is controlled by a pressure pad or button that can be activated by the patient. It is the method of choice for patient-controlled analgesia (PCA).

Parenteral Nutrition usually requires an infusion curve similar to normal mealtimes.

Patient-controlled Epidural Analgesia (PCEA) is a related term describing the patient controlled administration of analgesic medicine in the epidural space, by way of intermittent boluses or infusion pumps. This is most commonly used by terminally ill cancer patients.

Although the use of infusion pumps for very small volumes of often very potent drugs has begun, the accuracy of infusion pumps is still an issue. A recent study of commercially available infusion pumps has found significant errors in delivery volumes. In some cases the amount delivered over a long periods, as is typically used in calibration, may be accurate to a few percentage. But the delivered volume over short time scales and delivery rates have been found to vary by as much as 50% from the target settings. Over-dosing or under-dosing can result in adverse short term responses to potent drugs and multiple requests for dosing. Significant variations in delivery volume with temperature have also been found. This has resulted in limiting the use of infusion pumps to therapies where the detrimental effects of overdosing and under-dosing are limited. Highly potent medications delivered in small volumes are not candidates for today's infusion pump technology.

The reasons for errors in delivery are several. Many infusion pumps use disposable syringes as the pumping chamber. These use single-use or disposable syringes and therefore, are ideal to avoid potential cross contamination of medication. However these type syringes vary and the force required to move the syringe piston, or plunger, a given distance to deliver a given volume may not be the same from one syringe to the next. This variation in force without a suitable feedback control system will result in errors in delivered volume. Additionally the delivery volume variations from current technology pumps have been found with changing temperatures. A main factor for this variation may also be changing viscosity of the medications with temperature. Delivery volumes are also affected by the back pressure or resistance to the injection. To take advantage of the infusion pumps' ability to deliver medications under pressure that enables subcutaneous injections and epidural injections requires careful control of the delivery volumes even with varying backpressure or resistance to injection offered in the biological environment. Other factors that are not yet understood may also be significant. There is a need for a system to ensure accurate and reproducible delivery volumes and delivery pressure (would this not be primarily delivery volumes—the pressure may vary depending on the actual parts so that delivery volumes are accurate; of course we could use force control as well to ensure accurate delivery pressures).

Additionally new mechanisms are being developed, or have been developed, to drive (administer) the injection (and/or infusion). Simplified mechanisms are being found that can deliver the dosages required using both gravity and spring driven pump mechanisms. These simple systems eliminate motor drives and the associated electronics and their high power consumption. These systems can offer new levels of reliability and compactness, with considerably reduced cost?. There is a need however for new control mechanisms.

Closed loop feedback control mechanism are known in robotics, mechanics and machine control. However these control methods are still missing from medical devices such as infusion pumps. Traditional servo motor drives include proportional integral and derivative position loop (PID) and proportional position loop integral and proportional velocity loop (PIV) feedback control schemes, as well as other non-linear control schemes. Hereinafter the aforementioned schemes will be referred to simply as "feedback control schemes" (does this sound ok—if not please feel free to use some other term). There is a need to develop such feedback control schemes for use with motor driven infusion pumps. Additionally the simple non-motor driven infusion mechanisms require control means that are equivalently effective. The known feedback control schemes, PID and PIV, do not necessarily apply directly to a non-motor driven pump system. New control schemes are required that delivery very small volumes accurately and reproducibly regardless of the method use to drive the pump. New schemes are required for a motor driven syringe, a spring driven syringe, a gravity feed, a spring bag, a peristaltic pump and others. The control schemes must be able to adapt to the unique sources of variation in the medical and biological application of infusion pumps. The control schemes must provide accurate delivery volumes over time with changing temperature, viscosity, back pressure and manufacturing variations in mechanism components.

The apparatuses proposed here can be used either directly, or with simple modifications, for all the different infusion methods used in the medical field. Note that the apparatuses presented here do not represent an exhaustive list, and are simply representative of the approach presented here. Apparatuses that can be derived by extension, by those skilled in the art, are therefore included in the intended scope of this application.

SUMMARY OF THE INVENTION

One embodiment of the invention includes a system architecture design for infusion pumps and several instantiations of that design are described. The system architecture enables closed-loop feedback control for a variety of infusion pump physical designs. The system architecture enables accurate and precise dosing over a range of dosage volumes and dosage rates. In one embodiment the architecture is used with low cost gravity fed infusion systems. In another embodiment the architecture is shown applied to a spring driven infusion system. In yet other embodiments the system architecture provides precise control for servo motor driven pumps. In one embodiment the pump is a syringe pump.

Other embodiments of the invention include integrated sensor mechanisms and controllers that can be easily attached to conventional intravenous infusion systems. An integrated drop counter and controller for a gravity fed intravenous system is provided. Another embodiment includes a controller and actuator that together provide a control mechanism that controls the flow by squeezing or releasing the exit tubing of the infusion mechanism. In one embodiment the controller receives a flow signal from a drop counter. In another embodiment the controller receives a flow signal from an encoder incorporated into or attached to a syringe plunger to detect and measure movement. In a preferred embodiment the control mechanism includes a solenoid actuated pincher. In another embodiment the tubing is squeezed by other mechanisms such as an offset cam mechanism.

In another embodiment a spring driven syringe includes feedback mechanisms for the volume and rate of dosage and further includes a controller that ensures precise and accurate rate of delivery through use of the feedback control schemes mentioned before. The syringe enables dosage where a higher backpressure might preclude use of a gravity fed system. In one embodiment the feedback system includes a magnetic sensor incorporated in the plunger of the syringe. In another embodiment the sensor is a magnetic plunger is coupled with an inductive coil to measure both the position and rate of movement of the plunger and therefore the delivery volume and rate. The measured volume and rate is used in a closed loop feedback system as per methods indicated previously. In another embodiment the inductive coil and magnetic plunger are also used to control the delivery rate by applying a current to the coaxial inductive coil. In another embodiment the inductive coil is incorporated in the barrel of the syringe. In another embodiment the inductive coil is mounted in an offset manner. In another embodiment the current used to drive the inductive coils is used as a measure of the pressure downstream of the pump. Other embodiments include capacitive, optical and other magnetic encoders to determine plunger position.

Other embodiments of the invention provide motor driven syringe pumps. In one embodiment linear motor driven pumps are provided. In another embodiment lead screw driven syringe pumps are provided. Combinations of position sensors for syringe plunger position, and optical, and other sensors, for flow, bubble and pressure are included into a closed loop control system for volume delivered and rate of delivery. In another embodiment the sensors further provide a fail safe system for malfunctions such as occlusions, leaks or disconnected tubing.

In another embodiment the drive mechanism is an external spring mechanism. A "off the shelf" syringe may be mounted into the mechanism to provide pump system. In another embodiment the external spring drive mechanism further includes sensors to detect and measure movement of the syringe plunger. In another embodiment the external spring drive mechanism further includes a controller and actuator to provide close loop feedback control of the flow from the syringe. In one embodiment the actuator is a solenoid driven mechanism that provides flow control by squeezing a flexible tubing attached to the exit needle of the syringe and thereby controllably restricting flow.

DETAILED DESCRIPTION

Figure 1:
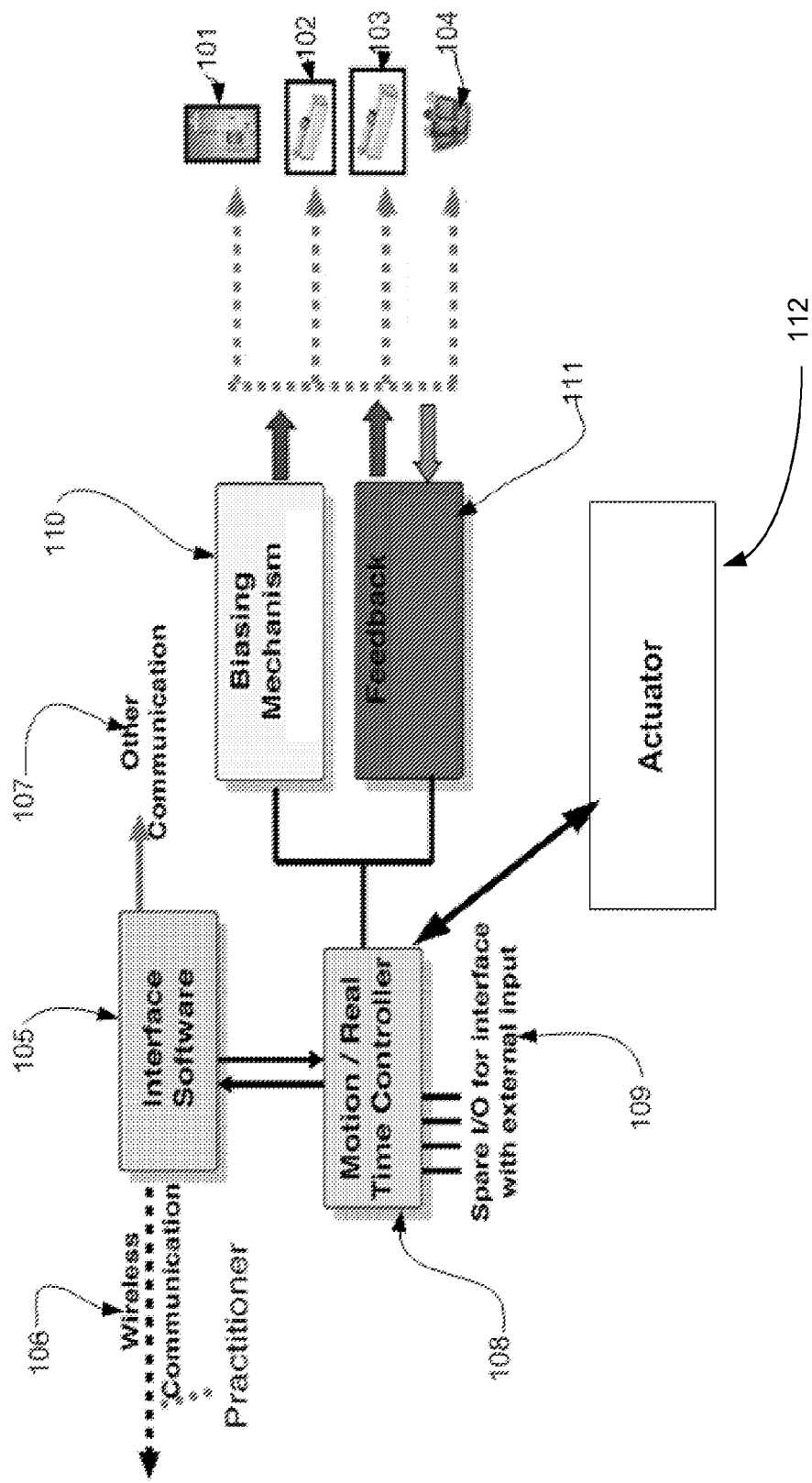
FIG. 1 is a block diagram of a system architecture embodiment.

Control of the flow from an infusion system is a key feature of the invention. A system architecture embodiment provides an outline of a means for closed loop feedback control of infusion pump systems. The architecture is shown applicable to simple low cost gravity driven systems and to servo motor driven systems. Generally speaking the architecture is applicable to the precise control of all infusion pumps where flow is created using a biasing force (eg, motor, spring, gravity and the like) and where a means of feedback that is a measure of the actual flow rate is provided. Physical embodiments of several syringe systems are shown. The control architecture applies to all pump embodiments and is in fact scaleable to other medical devices as discussed below. The architecture is modular and scaleable. It consists of a real time controller that provides precise, accurate, closed loop control of the flow. The term "Biasing Mechanism" in the following discussions refers to all possible methods of fluid pumping actuation used to accomplish infusion, non-limiting examples include gravity, biasing spring, linear motor, ball screw, inductive coil, solenoid, and voice coil actuator. Similarly the term "Feedback" refers to all methods of obtaining feedback on the actual flow, non-limiting examples include optical encoder, magnetic encoder, capacitive encoder, inductive encoder, through beam sensor for counting drops, and pressure drop measurements that can be converted to flow. A real time controller closes the loop between actuation signal and feedback signal to obtain a precise and accurate flow. The system can also regulate an arbitrarily specified flow profile. Another embodiment of the real time controller includes input and output (IO), which can be both digital and analog in nature. This IO allows for addition of limits switches, safety switches, patient input, interface, both closed loop or open loop, with other medical devices in the hospitals and programming of infusion strategies based on the same, optimization of system performance. In one embodiment the control uses PID or PIV control of motor based biasing mechanisms to reach a target infusion based upon selected parameters and feedback from sensors of flow, pressure or other parameters. One embodiment includes closed loop control of fixed biasing mechanisms. Exemplary fixed biasing mechanisms include gravity and springs. Springs include a spring driven syringe plunger as well as springs used to compress supply bags thereby inducing pressure into the system that drives the fluid flow. Another embodiment uses elastomeric supply bags that squeeze the fluid out by means of the elasticity of the material that the bag is made of. In another embodiment rubber bands or collars, or bands and collars of other elastomeric material are used to provide the biasing mechanism. In another embodiment the biasing mechanism includes spring loaded rollers that squeeze the bag.

Another embodiment includes a communication interface between the real time controller and the external devices, which may be wired or wireless. Non-limiting examples of external devices include cell phones, PDAs, laptop computers, desktop computers, and teach pendants that are used to communicate with the controller to report infusion parameters and to set infusion parameters. These external devices can be used for programming of the pump, data logging of critical parameters, monitoring and providing external intervention in pump operation if needed. Note that the communication interface may either reside on the real time controller, or on a separate controller if so required. The communication interface can also be used to integrate the pumps to the hospital management systems, enterprise resource planning systems, customer relations management systems, etc. Note that the control architecture presented can be applied to any medical device as such. It also therefore represents a general controller for medical devices.

Another embodiment includes a sensor and controller for gravity feed intravenous systems. The sensor controller can be attached to conventional systems without modification. The sensor controller consists of a through beam emitter and receiver that is mounted relative to a reservoir and a means to compress the connecting tube as a means of regulating flow. In a preferred embodiment the means to compress the tube is a solenoid. In other embodiments nonlimiting examples of the means to compress the tube include a motor, pneumatic means, hydraulic means, and peristaltic means. The following discussion in this section will be restricted to a solenoid without loss of generality, with the understanding that the following discussion in this section also applies to the other means of actuation described. The solenoid and sensor are parts of a closed loop control system.

Several pumping embodiments are also provided. In a first embodiment a spring driven syringe uses a mechanism to pinch exit tubing from the syringe. The flange of the barrel of the syringe of the syringe is fit with a sensor means to determine the position of the syringe plunger. In one embodiment the sensor means includes magnets embedded in the plunger body and a reader attached to the barrel assembly of the syringe. The sensor means provides a measure of the position of the plunger relative to the barrel of the syringe and therefore the volume that has been delivered and the rate of delivery. This measure is used in a closed loop control system with the means to constrict the exit tube from the syringe to control flow. Because the biasing mechanism for the syringe is a spring the closed loop system accounts for changes in the spring force as the spring is relaxed as the plunger enters further into the barrel. The size of the spring is selected such that, at any position of the plunger, there is sufficient biasing force to provide the maximum flow rate that might be required of the system.

Another embodiment of a syringe pump includes a ferromagnetic piece attached to the plunger on a spring driven syringe pump. The ferromagnetic piece is enclosed within an inductive coil. The movement of the ferromagnet through the inductive coil provides a sensor means for the position and movement of the magnet and therefore delivery of the fluid as the attached plunger moves into the syringe barrel. The sensor is then coupled with a means to constrict the exit tube from the syringe and a controller to provide a closed-loop control system. Another embodiment incorporates the inductive coil into the barrel of the syringe thus providing a more compact system. In another embodiment a current is applied to the inductive coil to provide an additional controlling force on the syringe plunger for closed-loop control. Another embodiment connects the ferromagnet and an induction coil to the syringe plunger but located offset from the axes of the syringe plunger and syringe barrel.

In other embodiments the means of feedback and actuation include an actuation means to control the exit flow that includes, instead of a solenoid compressing a tube, flow regulation through a variable orifice, a flow valve, a needle valve, and the like. In other embodiments the biasing mechanism to provide the biasing pressure for pumping fluids includes other means, including but not limited to extension springs, electromagnetic means, magnetic means, pneumatic means, hydraulic means and elastomeric means.

In another embodiment sensing the plunger position and motion in a syringe is provided by capacitive means. The plunger is embedded with a good dielectric material, or may itself be made of a good dielectric material. A pair of parallel electrodes are positioned so that some section of the plunger containing the dielectric material is always between the parallel electrodes such that the electrodes are partially blocked by the aforementioned plunger section. As the plunger moves the amount of dielectric between the electrodes changes. The position and velocity of the plunger is measured by measuring the capacitance across the electrodes. In another embodiment the plunger position and motion is determined by optical means. Exemplary optical means include an encoder tape, consisting of gratings, mounted on the plunger and an optical read head may be mounted on the barrel flange, permitting real time measurement of position and velocity.

In other embodiments the syringe is driven by conventional servo motors and associated controls. The mechanisms may be rotary motors attached to ball screws or lead screws. In these cases rotary encoders may be attached to the motors for closed loop control of the motor motion. Motors may also be linear drive motors. Additionally sensors described in association with other embodiments may be incorporated. Such sensors include drop counters for volume measurement and linear position detectors for the location of the syringe plunger. The combination of sensors are incorporated into the feedback mechanism for accurate and precise volume delivery. The motors also provide additional feedback in the form of indirect pressure measurement. The current load required to drive the motor is an indicator of the back pressure for fluid delivery. The load measurement may be further included in closed loop control. In another embodiment the load on the drive motor is used as a fail-safe indicator of occlusions or leaks or broken tubing.

System Architecture

FIG. 1 depicts a block diagram for the system architecture. The architecture is applicable to and includes an interface to at least one of an infusion pump system selected from drip systems 101, spring driven syringe pumps 102, motor driven syringe pumps 103. In another embodiment the system architecture may be applied to other hospital systems 104 benefiting from closed loop feedback control. Non-limiting examples include control of a medical robot using a multiple axes version of the controller, control of a system where feedback from body, eg blood pressure—has to reach a certain value, and the controller uses this feedback to control a system such that the pressure reaches and maintains a target value, Similar systems may use heart rate as the feedback sensor. The system further comprises an interface software 105 which provides the control algorithms for the controller 108 as well as communication interfaces to users 106, 107. The communication interface between the real time controller and the external devices may be wired or wireless. Non-limiting examples of external devices include cell phones, PDAs, laptop computers, desktop computers, and teach pendants that are used to communicate with the controller to report infusion parameters and to set infusion parameters. These external devices can be used for programming of the pump, data logging of critical parameters, monitoring and providing external intervention in pump operation if needed. Note that the communication interface may either reside on the real time controller, or on a separate controller if so required. The communication interface can also be used to integrate the pumps to the hospital management systems, enterprise resource planning systems, customer relations management systems.

The controller 108 is a hardware element that provides drive signals to the biasing mechanism 110 in the case of motor driven syringe systems and control signals to actuation means 112 to control features such as hose pinching devices or other means to regulate flow. Biasing mechanism refers to all possible methods of fluid pumping actuation used to accomplish infusion, non-limiting examples include gravity, biasing spring, linear motor, ball screw, inductive coil, solenoid, and voice coil actuator. A feedback means 111 provides signals related to flow, pressure and other system controlled responses to the controller. Feedback refers to all methods of obtaining feedback on the actual flow, non-limiting examples include optical encoder, magnetic encoder, through beam sensor for counting drops and pressure transducers. In another embodiment feedback may also be an indirect measure of response such as the load required to drive a motor to attain a selected rate of movement of a syringe plunger. The rate of movement of the syringe plunger is provided by position sensors such as magnetic, optical, capacitive or other sensors linked to the syringe plunger. The motion controller includes further I/O interfaces 109 for use with external alarm systems or other external input such as patient monitoring equipment. This IO allows for addition of limits switches, safety switches, patient input, interface (either closed loop or open loop) with other medical devices in the hospitals and programming of infusion strategies based on the same, optimization of system performance.

In another embodiment the encoder feedback error is used as an inferred measure of the force required to infuse the liquid. The inferred force along with the flow are then used in a closed loop control system. The encoder feedback error is given by equation 1.

$$\in(x) = X - X_0 \qquad \text{eq.(1)}$$

where $\in$ is the error in the encoder position, X is the actual encoder position and $X_0$ is the target encoder position. The target values $X_0$ are a function of time. The infusion program is a program to deliver a volume per unit time or a total volume infusion period of time. The infusion program may also include programmed variations in rate of infusion over the total time that the infusion is taking place. The position X and X0 are directly proportional to the volume remaining in the syringe and by difference the volume delivered. In a single parameter closed loop system X is periodically measured, the error $\in(x)$ is calculated and an actuator potential is adjusted to minimize the error. The error $\in(x)$ is also proportional to the resistance to infusion or the force required to infuse the fluid. In another embodiment the error $\in(x)$ is also programmed in the infusion program such that both the pressure and the volume delivered are controlled along a selected trajectory. In one embodiment the interface software programs the controller to use PID or PIV control of motor based biasing mechanisms to reach a target infusion based upon selected parameters and feedback from sensors of flow, pressure or other parameters. Another embodiment includes closed loop control of fixed biasing mechanisms. Exemplary fixed biasing mechanisms include gravity and springs. Springs include a spring driven syringe plunger as well as springs used to compress supply bags thereby inducing pressure into the system that drives the fluid flow.

Sensor-Controller

Figure 2:
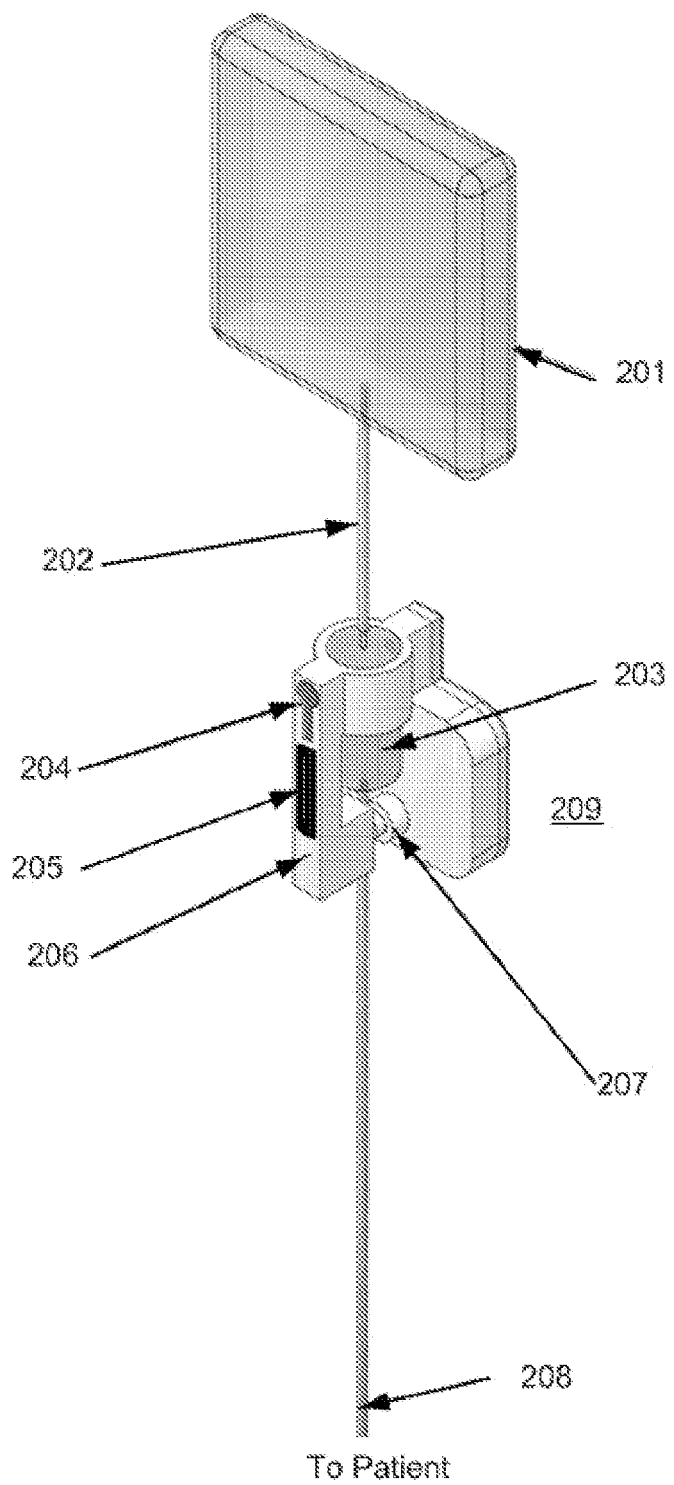
FIG. 2 is a diagram of an integrated flow sensor and control unit embodiment.

Referring now to FIG. 2, another embodiment includes a combined sensor and controller 209 for intravenous systems. The sensor-controller 209 can be attached to conventional systems without modification. The sensor controller is placed in line between the supply means 201 and the tube that connects to the patient 208. The sensor-controller consists of a through beam emitter and receiver 204 that is mounted relative to a reservoir 203 and a means to compress the connecting tube 207 as a means of regulating flow. In a preferred embodiment the means to compress the tube is a solenoid. In other embodiments the means to actuate the solenoid and compress the tube is a motor, pneumatic means, hydraulic means. In other embodiments the means to compress the tube includes a mechanism or transmission (such as roller, linkage, gears, etc) driven by any of the aforementioned means of actuate the solenoid may also be used. The sensor-controller further includes integrated electronic controls 206. The sensor controller may also optionally include a means 205 to measure the fluid level within the chamber 203. The flow out of the sensor-controller is equal to the flow measured by the drop sensor minus the volume accumulated in the sensor-controller as measured by the level sensor. The following discussion in this section will be restricted to a solenoid without loss of generality, with the understanding that the following discussion in this section also applies to the other means of actuation described. The solenoid and sensor are parts of a closed loop control system.

In another embodiment the supply means 201 from which the fluid enters the sensor-controller is any of a spring loaded container, a container where fluid is pressurized, a pneumatically loaded container, a container where fluid is expelled through mechanisms such as a ball screw or a lead screw or rack and pinion or rollers, a container where fluid is expelled by magnetic means, electromagnetic means and the like. Fundamentally the container may expel fluid through a wide variety of means including any of those listed above.

Figure 3:
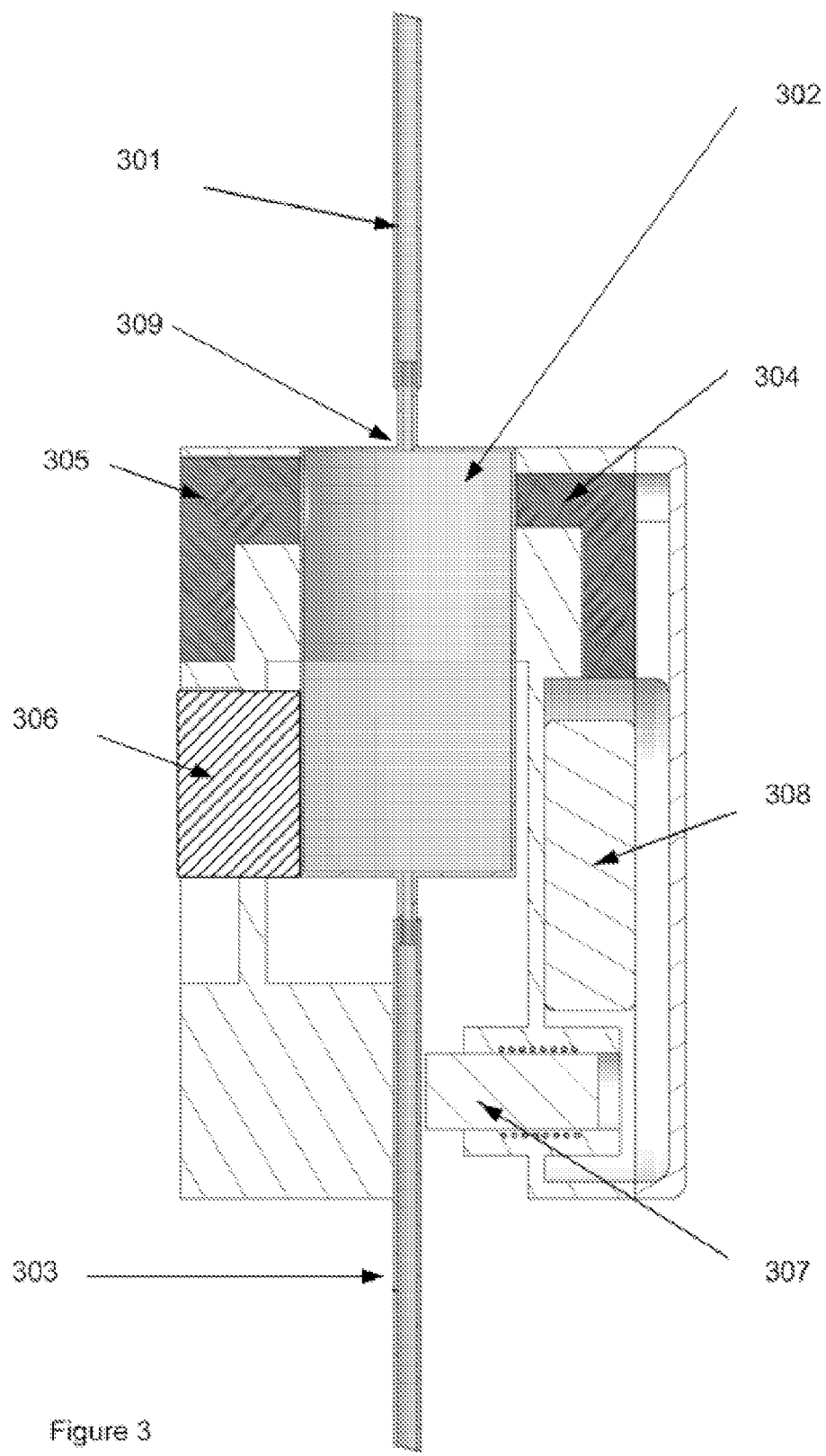
FIG. 3 is a detail cross-section view of an integrated flow sensor and control unit embodiment.

FIG. 3 depicts a detailed cross sectional view of the components of the sensor-controller 209. A tube 301 connects to the supply means. Fluid from the bag enters the reservoir 302 through an orifice 309 in the form of drops. The sensor-controller automatically regulates the flow of the fluid as follows. Each time a drop of the fluid enters the reservoir, it breaks the beam from a light emitter 304 to a light receiver 305. Exemplary light emitters would include a light emitting diode and exemplary light receivers would include a photodiode. The signal at the receiver 305 drops to a low value when the leading edge of a drop (which is the first edge of the drop) breaks the sensor beam and then goes back to a high value when the trailing edge of the drop is clear of the sensor beam. The aforementioned change in signal at the receiver is hereafter referred to as a pulse. The frequency of drops, measured by measuring the frequency of the pulses, corresponds to the volume flow rate (i.e. volume flow rate is frequency of drops multiplied by the volume per each drop). In one embodiment the system compensates for variations in drop volumes using the pulse width. The width of each pulse in time, is representative of the volume of each drop and is used for purposes such as, but not limited to: calculating the volume per drop, compensating for variations in drop size due to for example viscosity or temperature. In another embodiment the sensor beam can be designed to be wide at the location where the drops break through so that the apparatus will function accurately even with large variations in the axis of the reservoir from the vertical axis (i.e. even if the reservoir is not held perfectly vertical). Note that the width of the beam is tailored using optics at the emitter and receiver. In another embodiment multiple emitters and receivers are used so that multiple beams are broken by each drop. This also provides for redundancy. In another embodiment, instead of separate emitter and receiver, a reflective sensor, with emitter and receiver in the same head, can also be used. In this case both the emitter and the receiver are contained in head 304 and a reflector is positioned opposite at 305. In another embodiment direct measurement methods of flow such as ultrasonic means, conventional flow measurement methods such as laminar flow meters, and the like may also be used in the apparatus presented here. In another embodiment the receiver signal may be analog in nature so that as the drop breaks the beam the variation in intensity at the receiver signal may be used to accurately reconstruct the shape of the drop resulting in even more accurate measurement of flow. In a further embodiment a vision system, such as a high speed CCD camera is used, along with a strobe light, to take pictures of the drops and compute the volumes by suitable processing of the image.

In another embodiment, an additional sensor 306, which may be a single sensor or an array of multiple sensors are provided to measure the level of the fluid, and variations of the same, accumulated in the reservoir 302. This can provide additional accuracy and confirmation of flow measurement by measuring any accumulation in the reservoir. If for some reason some accumulation of flow occurs during input from this sensor can be used along with the frequency and size of drops to accurately compute the flow rate and use the same as part of the feedback control system.

Embodiments of the sensor-controller further comprise a solenoid 307 that may be actuated to squeeze or release the exit tubing 303 to control the flow. The sensors and actuators are controlled by integrated electronics 308.

Flow control is accomplished with use of closed loop control algorithms where the flow set point is calculated to be a drop rate, or frequency, using a nominal drop volume. Both drop counts and drop size are measured. The nominal drop volume is adjusted based upon measurements of actual drop volume and the flow rate is calculated and compared with the set point. The solenoid 307 compresses or releases the tube 303, depending on the frequency of pulses, to reach the desired flow rate.

In another embodiment the drop sensor-controller described is integrated with the motors used in pumps such as peristaltic pumps and others to provide an accurate closed loop peristaltic pump. Similarly the drop sensor can be integrated with other forms of infusion (such as diaphragm pumps, bellows, elastomeric bags, etc) to form accurate close loop infusion pumps.

In another embodiment the drop sensor alone, the through beam and optionally the accumulation sensor, is used as an aid for the regular bag intravenous infusion system. Instead of using a watch and counting drops while adjusting the normally used roller, the practitioner uses a display that is showing the frequency of drops and manually adjust roller position so that the drop frequency and therefore flow rate is adjusted to the target value.

In another embodiment the entry orifice 309 is a variable orifice. The purpose of this second variable orifice is to vary the size of the drops entering the reservoir. For highly accurate flow rates, it would be possible, using this approach, to minimize the volume of each drop so that the number of drops per unit of flow is maximized, resulting in higher resolution of the system, which in turn results in greater accuracy.

Figure 4:
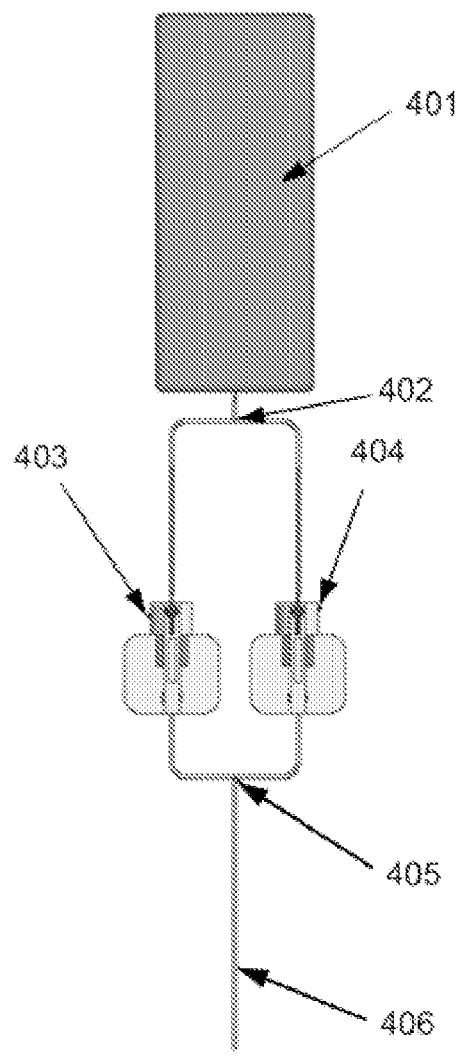
FIG. 4 is a diagram showing an embodiment using multiple flow sensor and control units.

Another embodiment, shown in FIG. 4, is used with infusion pumps that can infuse large volumes, 1 liter per hour or more. Quite often solutions to accomplish large volume infusion are accomplished using larger diameter tubing and larger orifices at the entry to the reservoirs. This results in larger drop sizes and hence lower resolution. Further there is also a physical limit on how large the tube and orifice diameters can be before drops no longer form at the entry to the reservoir. The aforementioned drop sensor-controller can be used for accurate infusion of large volumes: the tubing from the supply means 401 is routed to two sensor-controllers 403, 404 using a T-junction 402, and the flow exiting from the drop counters is merged into one stream using another T-junction 405. The arrangement shown in FIG. 4 thereby permits doubling of the flow without affecting the resolution of the system and the accuracy of the system. The approach is not restricted to just two drop counters. In another embodiment a plurality of sensor-controllers is used to increase the maximum flow rate of the system without compromising resolution and accuracy.

In another embodiment, not shown, a single actuator to squeeze the tube downstream of the downstream T-junction 405, is used, instead of individual actuators for each of the tubes exiting the reservoirs. In this case the flows measured at each of the reservoir is summed up and used as the total flow and the actuator is used to squeeze the exit tube to control the total flow.

In another embodiment a single reservoir 302 of FIG. 3, is fit with multiple orifices and drop sensors. This would correspond to multiple flow streams coming through multiple orifices 309 into one reservoir body 302. Referring to FIG. 4 this would correspond to the case where all the sensors and tubing remain as shown and the two reservoirs would merge into one reservoir that encompasses the two reservoirs shown.

Spring Biased Syringe Pump

Figure 5:
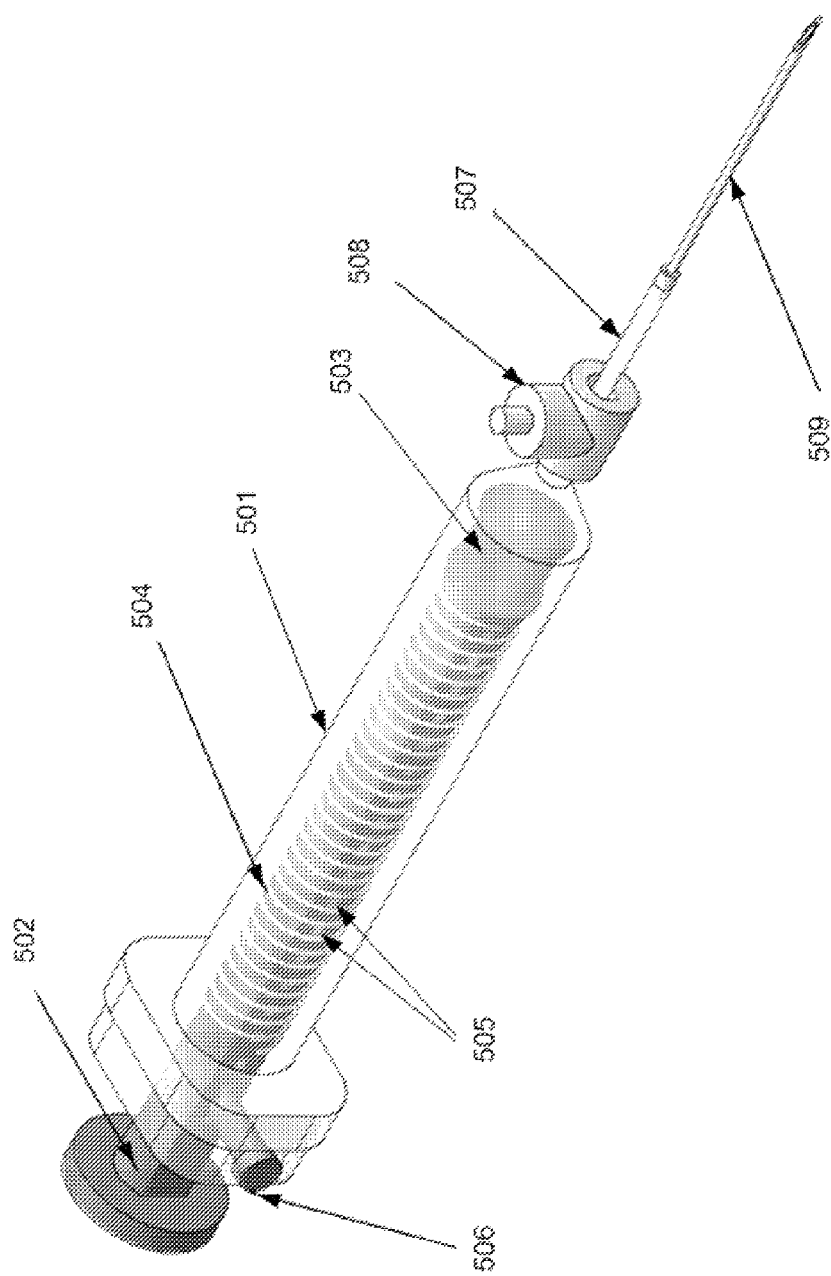
FIG. 5 is a diagram of a spring driven syringe embodiment.
Figure 6:
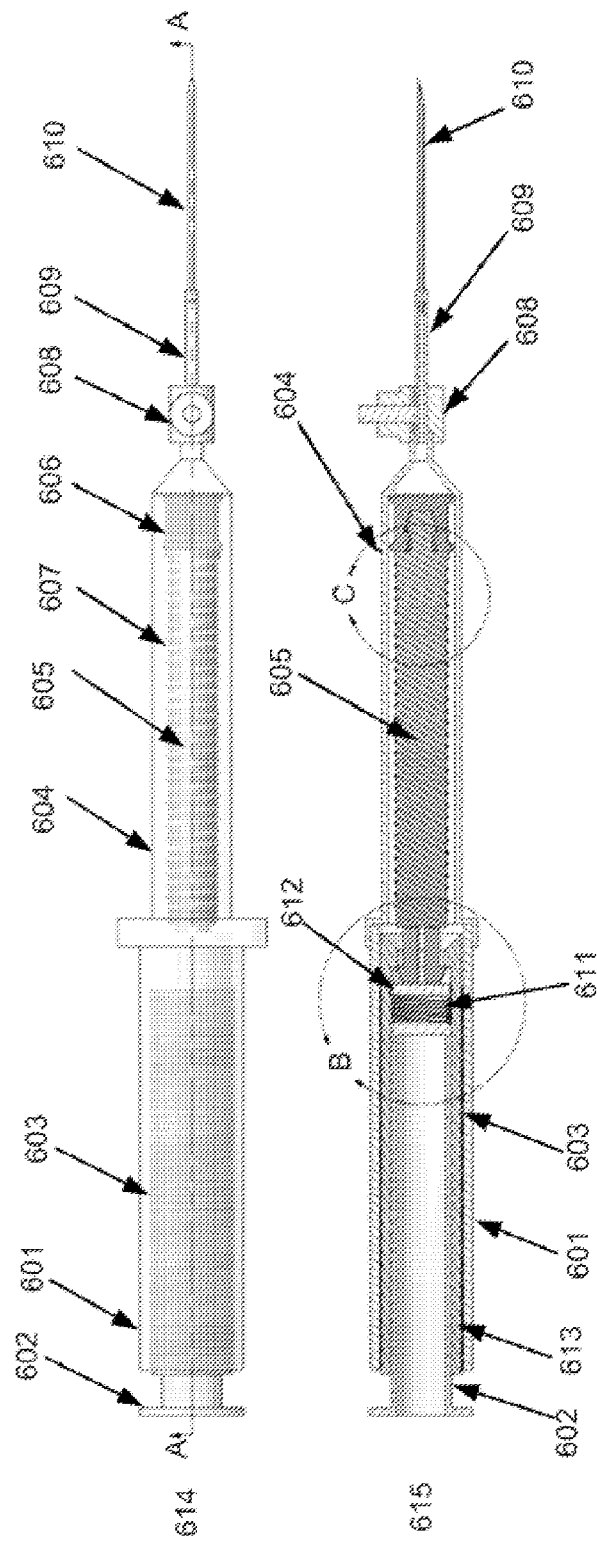
FIG. 6 shows cross-sectional and more detailed views of an embodiment incorporating a ferromagnetic plunger and inductive coil.

Another embodiment is shown in FIGS. 5 and 6. A closed loop infusion pump is comprised of a spring biased syringe with integrated sensors and a flow control means. The infusion pump consists of a spring biased syringe comprised of a syringe barrel 501 and plunger 502. The plunger terminates in a syringe gasket 503 to produce a fluid tight seal between the plunger and the syringe barrel. The syringe is driven or biased by a spring 504. Fluid contained in the syringe barrel is expelled out of the syringe through a compressible tube 507 and a delivery tube or needle 509. A series of magnets 505 are embedded in the plunger of the syringe. The flange of the syringe barrel is equipped with a magnetic read head 506. A compressible tube 507 is attached to the syringe tip and a solenoid 508 or like actuator is used to compress the tube to control the flow.

The pump operates as follows. The compression spring 504 is sized so that, with a fully open orifice corresponding to a fully open compressible tube bore 507, provides the maximum flow required by any application for which the pump may be used. The speed and position of the plunger 502, which are used to measure the rate of flow and the volume of fluid infused, is sensed by measuring the signal obtained at the read head 506 as the embedded magnets pass the read head. The aforementioned signal is the feedback signal (111) shown in the system diagram in FIG. 1 and is essentially a sinusoidal voltage or current signal, depending on the type of electronics used to condition the signal. This sinusoidal signal is applied to controller (108) shown in FIG. 1 and is a very accurate indicator of the position of the plunger. Note further that this sinusoidal signal can also be interpolated by controller (108) for further accuracy as in the case of commonly used sine-cosine encoders and inductive encoders. The flow is regulated by using the solenoid 508 as the actuator (112) shown in FIG. 1 to compress the compressible tube 507 attached to the tip of the syringe thereby restricting the flow from the syringe. The solenoid actuation signal and the position and velocity feedback from the plunger with magnets along with the controller form a closed loop system to give extremely good control and accuracy.

Spring Biased Syringe Pump and Ferromagnetic Sensors

Figure 7:
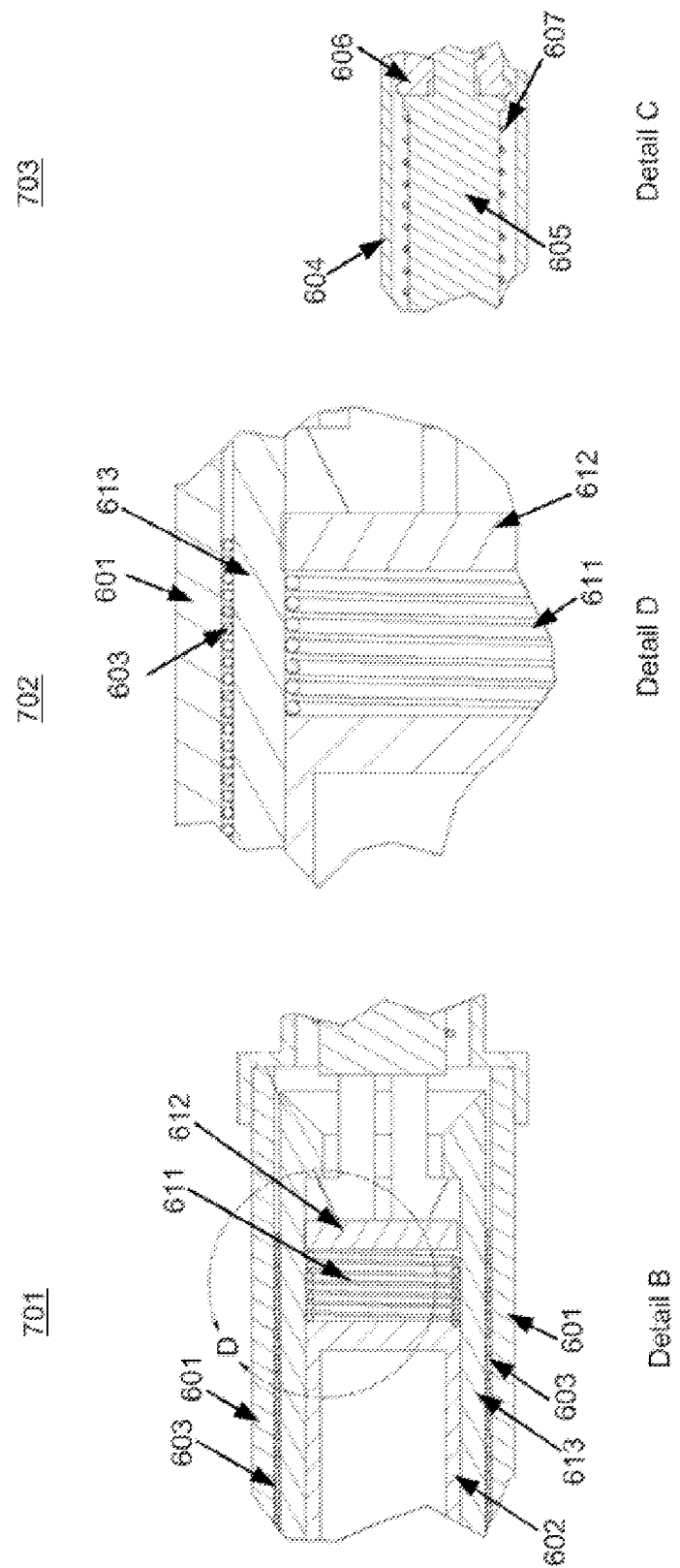
FIG. 7 shows close-up cross-sectional views of an embodiment incorporating a ferromagnetic plunger and inductive coil.

Another embodiment, shown in FIGS. 6 and 7, consists of a spring biased syringe with a compressible tube attached to the tip of the syringe as in the embodiments already discussed. A syringe with a syringe body 604, plunger 605 ending with a gasket on the plunger 606 employs a spring biasing mechanism 607 to drive the plunger and expel fluid from the syringe through flexible tubing 609 and a needle 610. Here too the flow through the syringe is regulated by using a solenoid actuator 608 mounted at the syringe tip to compress the compressible tube 609 attached to the syringe tip thereby restricting the flow from the syringe. However, instead of the plunger with embedded magnets, in this case the position of the plunger is sensed by attaching a ferromagnetic piece 613 to plunger extension 602 hereinafter referred to as the "magnetic plunger". The magnetic plunger is mounted coaxially within an inductive coil 603 which is housed in and attached to an extension 601 of the barrel 604 or a part attached to the barrel, as shown in FIGS. 6 and 7. The position and speed of the plunger 605 of the syringe, indicative of the volume of fluid infused and the volume flow rate, is measured by measuring the inductance of the inductive coil 603 using the controller (not shown), which varies depending on the position of the magnetic plunger 602 in the coil. As in the case of the other embodiments, the actuation signal applied to the solenoid by the controller and the signal from the inductive coil which is applied to and processed by the controller and corresponds to the inductance of the coil which is indicative of the volume of fluid infused and the volume flow rate, form a closed loop feedback system resulting in highly accurate and precise fluid delivery.

In another embodiment, in addition to acting as a position feedback the magnetic plunger 602 can also be used to add to, or reduce, the biasing spring pressure by applying a suitable amount of current (on top of that used to measure the inductance). This allows for further regulation/control of flow (in addition to that provided by the solenoid actuation). In another embodiment the magnetic plunger is also equipped with a permanent magnet 612.

In another embodiment, not shown, instead of mounting the inductive coil in a part on top of the syringe, the inductive coil is mounted directly on the syringe barrel, and the plunger of the syringe itself is a ferromagnetic piece.

Figure 8:
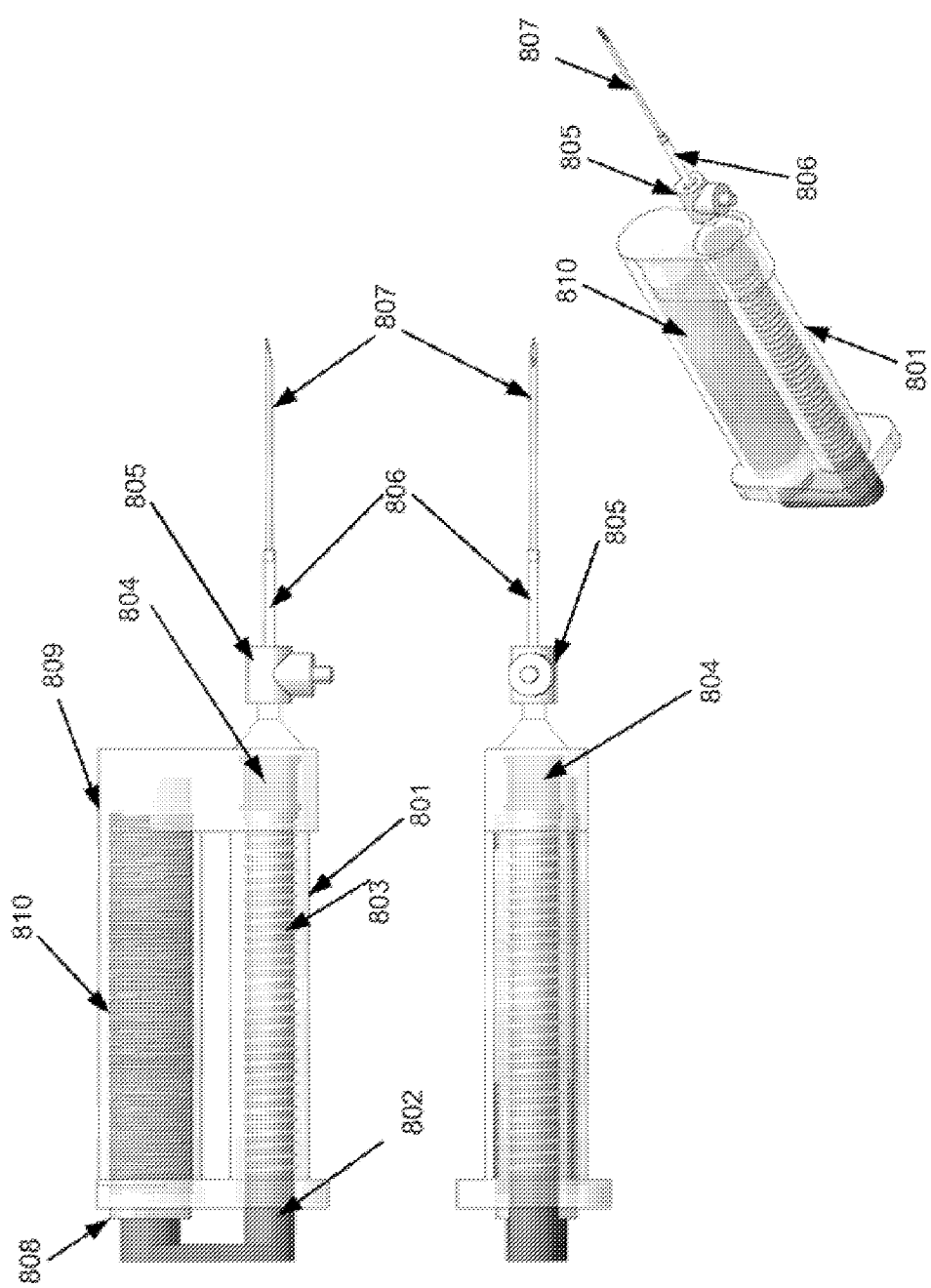
FIG. 8 shows a syringe embodiment with an inductive coil mounted in an offset manner.

In another embodiment shown in FIG. 8, the inductive coil is mounted in an offset manner. A syringe consisting of a syringe body 801 plunger and gasket 804 and spring biasing mechanism 803 has the plunger connected 802 to a magnetic plunger 808 which travels within the inductive coil 810 held within a second body 809 side by side with the body of the syringe. The embodiment further includes a flexible tubing 806 at the exit of the syringe that feeds into a needle 807 or other suitable tubing to delivery the fluid to the patient. The flow is controlled by a solenoid actuator 805 that can pinch the flexible tubing 806 to reduce flow.

In another embodiment, in addition to acting as a position feedback the magnetic plunger 808 can also be used to add to, or reduce, the biasing spring pressure by applying a suitable amount of current (on top of that used to measure the inductance). This allows for further regulation/control of flow (in addition to that provided by the solenoid actuation).

In another embodiment the magnetic plunger is also equipped with a permanent magnet.

In another embodiment the current required to drive the inductive coils can be used to monitor pressure changes in the tubing downstream of the pump.

Figure 9:
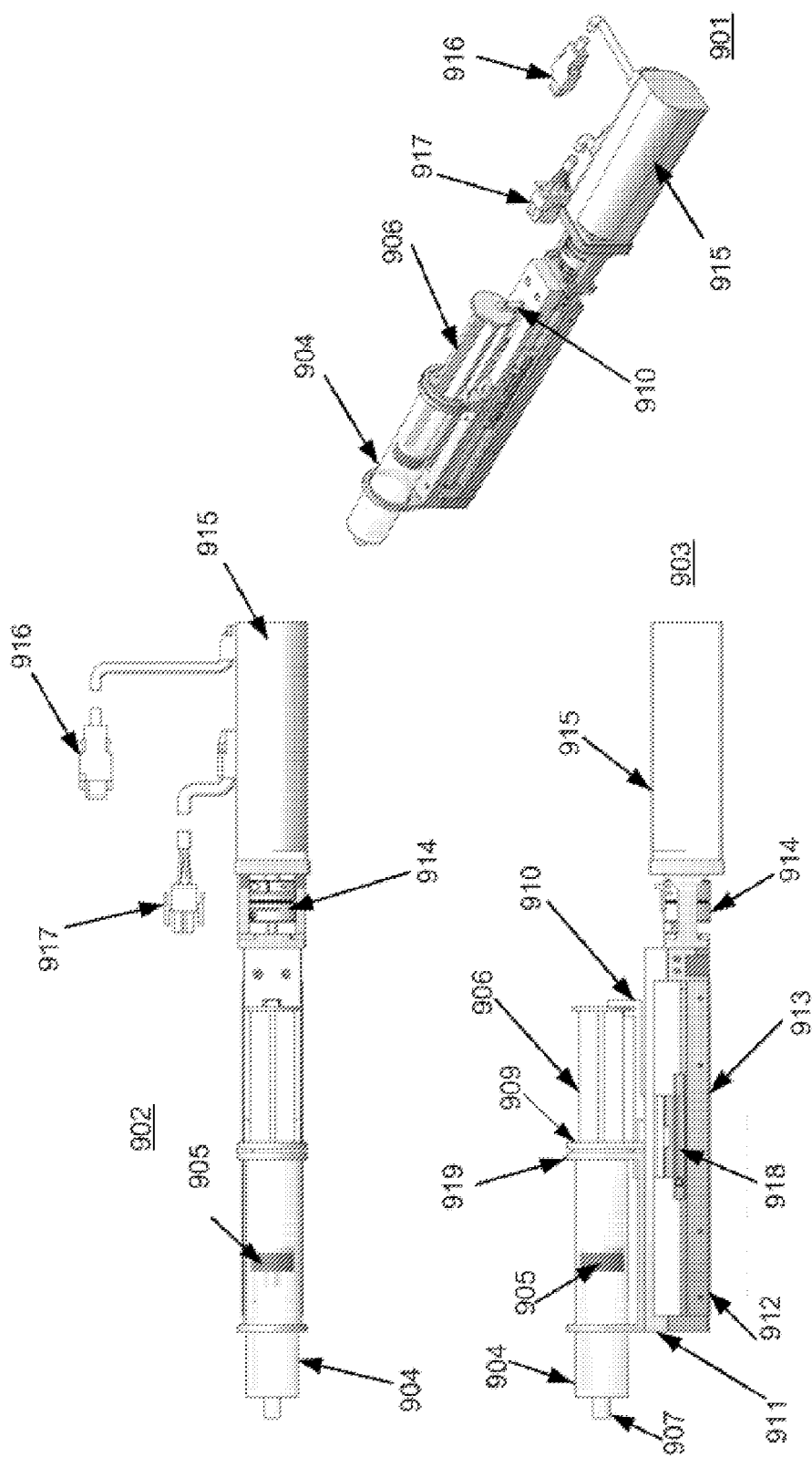
FIG. 9 shows a lead screw driven syringe embodiment.

The described system architecture is also used in providing closed loop feedback controls to motor driven syringes. Both rotary motor driven syringes with a lead screw assembly and linear motor driven syringes may be used. In one embodiment, shown in FIG. 9, a syringe is mounted using brackets 919 on to the ball screw and guide assembly 911. The plunger of the syringe 906 is driven relative to the barrel 904 by rotation of a rotary motor 915, which could be AC servo, DC servo, stepper motor and the like. The motor is equipped with a rotary encoder 914 that allows closed loop control of the motor. This in turn allows accurate control of the plunger movement and results in accurate infusion. For even more accurate close loop control an encoder may be mounted on the bracket 912 on which the ball screw and linear guides are mounted, with the encoder read head 918 being mounted on the (movable) bracket to which the plunger is attached.

In a preferred embodiment, the pitch of the ball screw is chosen to be typically in excess of 10 mm, so that the ball screw can be back driven. This arrangement results in the motor being more sensitive to changes in load at the output of the ball screw. This permits detection of pressure changes in the barrel of the syringe by noting the changes in the following error of the motor. The following error is determined by comparing the actual and commanded position of the motor. In another embodiment pitches less than 10 mm are used for the ball screw if the pressure requirements of the application mandate it.

Linear Motor Driven Syringe Pumps

Figure 10:
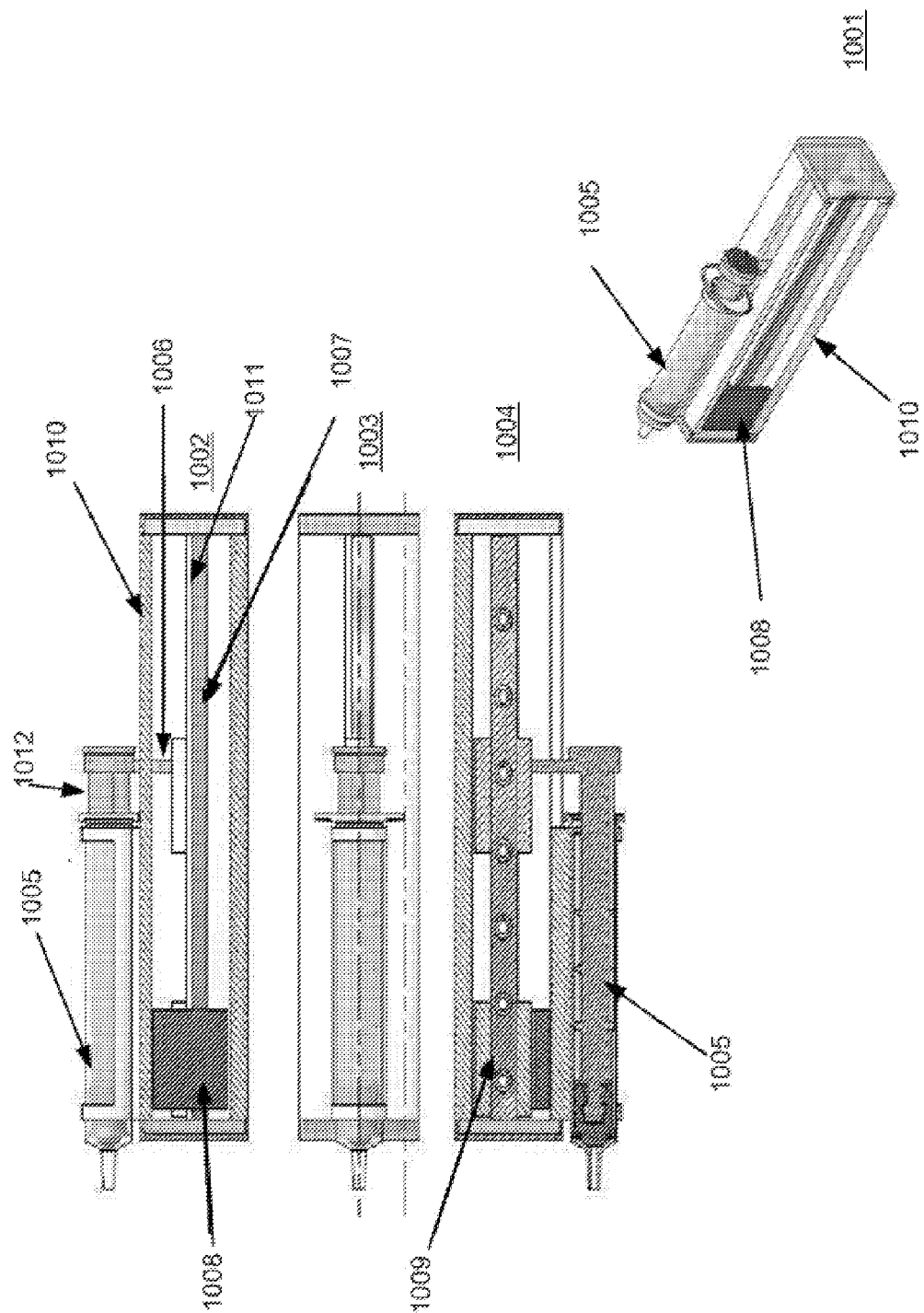
FIG. 10 shows a linear motor driven embodiment.

In another embodiment a linear motor is used as the biasing mechanism. FIG. 10 shows plan 1004 isometric 1001 top 1003 and elevation 1002 views of a linear motor driven syringe pump. A linear motor consists of a carriage 1006 including permanent magnets and fixed stator 1011 mounted in a fixture 1010. Appropriately feeding current in the coils causes movement of the carriage 1006. For stiffness, stability and accuracy the carriage is also guided using linear guides 1009 as illustrated. The syringe plunger 1012 is attached to the carriage 1006. Real time feedback of syringe position, velocity and acceleration are provided by mounting an encoder 1007 fixed relative to the linear motor stator 1011. The encoder read head 1008 is fixed relative to the carriage 1006 and hence to the syringe plunger. This encoder arrangement enables very accurate closed loop control of the flow. The encoder can be of various types nonlimiting examples include an optical sensor encoder read head and an optical encoder strip, and similar combinations of magnetic, inductive, and capacitive sensors and magnetic, inductive and capacitive encoders.

In another embodiment the pressure in the barrel is characterized by monitoring the following error of the linear motor, the following error being the difference between the commanded and actual position of the linear motor.

In other embodiments the position of the encoder and read heads are varied. In one embodiment, not shown, the encoders is mounted directly on the plunger of the syringe, which is the moving part. In another embodiment the encoder is mounted directly on the plunger and the read head is mounted in a stationary position on the stator of the motor. In another embodiment the read head is mounted on the barrel of the syringe which is stationary The linear motor variation is operated with a similar feedback control systems as already described. The difference is that the biasing mechanism in this case is a linear motor. The biasing mechanism may therefore be controlled. The control previously provided by the variable orifice, is replaced by a linear motor. Note however that the linear motor allows for the ability to drive the plunger in both directions, while the compression spring of course allows biasing force in only one direction.

In another embodiment, not shown, a voice coil actuator is used for the biasing mechanism instead of a linear motor. The moving part is a coil and the stationary part has magnets.

In other embodiments the magnets that are part of the stator and coils are integrated into the carriage.

Lead Screw Syringe Pump

Figure 11:
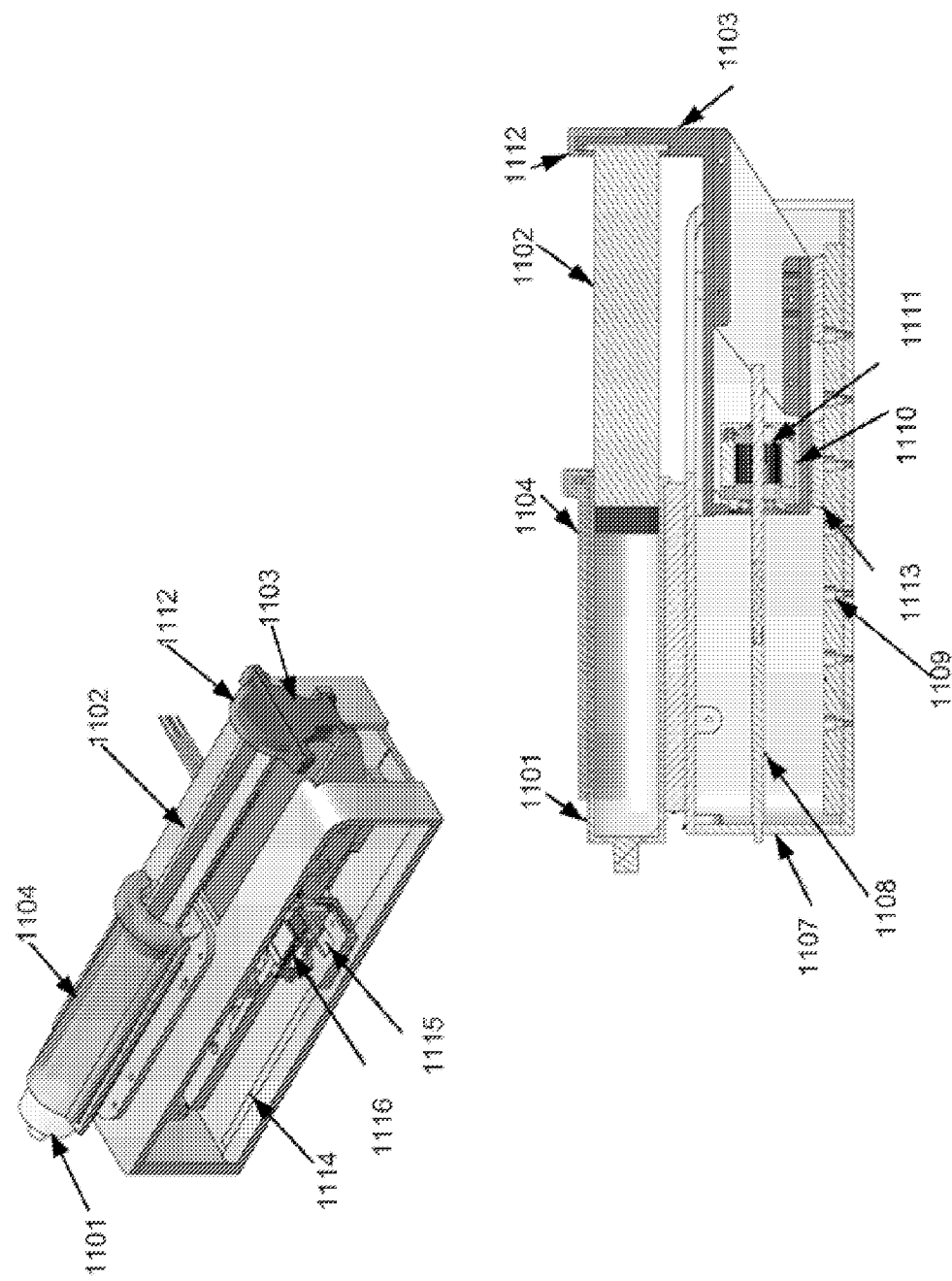
FIG. 11 shows a lead screw with fixed lead screw and moving motor embodiment.

Another embodiment is shown in FIG. 11. A syringe 1101 is mounted to a fixture 1107 by clamping the syringe barrel 1104 in a fixed position relative to the fixture. The syringe plunger 1102 is also clamped 1112 to a movable means 1103 that is attached to a motor 1110. The rotor 1111 of the motor engages a lead screw 1108 such that rotation of the motor drives the motor and therefore the syringe plunger relative to the syringe barrel thus discharging fluid from the syringe. The motor is attached to a movable carriage 1113 that rides in a guide 1114 to provide the ability to accurately move the syringe plunger with minimized error. The position of the motor and therefore of the syringe plunger is detected by a read head 1115 that is attached via a bracket 1116 to the same bracket that holds the syringe plunger. The read head senses magnets 1109 that are fixed in position relative to the moving motor and syringe. In another embodiment the position read head 1115 and magnets 1109 are replaced by other position sensing means. Non-limiting examples of such means include optical, magnetic, inductive, and capacitive devices.

External Spring Driven Syringe Pump

Figure 12:
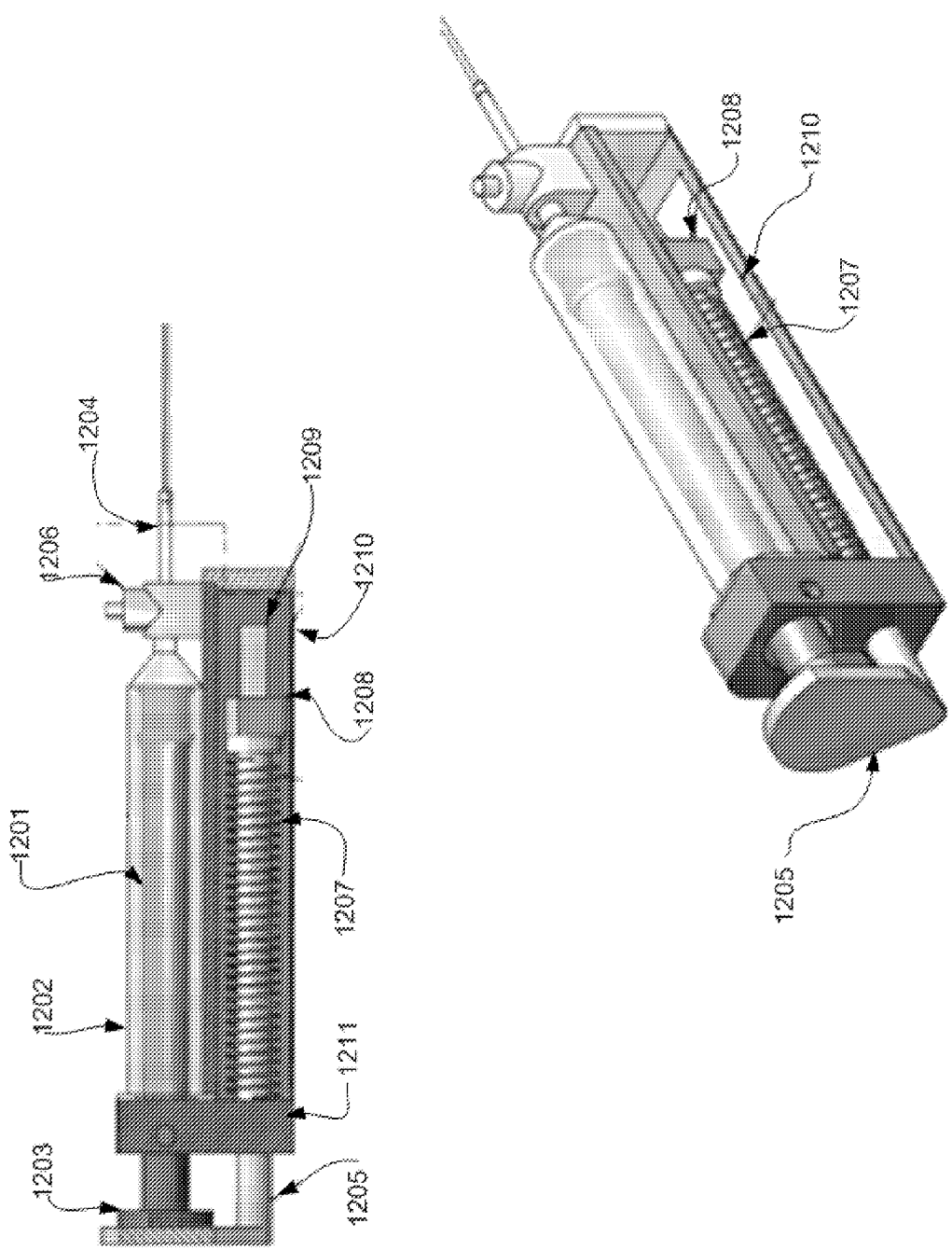
FIG. 12 shows multiple views of an external spring drive mechanism.

In another embodiment the biasing mechanism is a spring incorporated into a mounting fixture such that standard off-the-shelf syringes may be used with a spring biasing mechanism. Referring to FIG. 12, a syringe 1201 is mounted in a fixture 1211 such that the barrel 1202 of the syringe is fixed relative to fixture. The plunger 1203 of the syringe is mounted to a bracket 1205 that is movable relative to the fixture and is driven by a spring 1207 biasing mechanism. A flexible tube 1204 is attached to the exit of the syringe and an actuator means 1206 is attached around the flexible tube such that the actuator, when activated, can controllably squeeze the flexible tube, thereby controlling the flow from the syringe. Also attached to the movable bracket 1205 is a position sensor means 1208 which can sense the position of the movable bracket and therefore the syringe plunger within the fixture by sensing the position sensor location relative to an encoding strip 1210. Non-limiting examples of such means position sensor and encoding strip include optical, magnetic, inductive, and capacitive devices. Closed loop control of flow from the syringe is obtained by sensing the position of the syringe plunger and minimizing the error between the measured position and a target position encoded in an infusion controller program. Flow is increased by opening the actuator 1206 and decreased by closing the actuator 1206 where closing means squeezing on the flexible tube 1204.

SUMMARY

A system architecture for closed loop control of infusion devices is described. The architecture provides means to control the flow from an infusion device as well as in some embodiments the pressure of the delivery. A variety of infusion systems are described that use the closed loop control architecture. In some embodiments the closed loop control may be adapted to current commonly used infusion means such as a gravity feed intravenous system. Other embodiments describe infusion pump system that use biasing or drive mechanisms of springs, elastomers, rotary and linear motors. Those skilled in the art will appreciate that various adaptations and modifications of the preferred embodiments can be configured without departing from the scope and spirit of the invention. Therefore, it is to be understood that the invention may be practiced other than as specifically described herein, within the scope of the appended claims.

What is claimed is:

1. An infusion pump for delivering a fluid comprising:
   a) a syringe having a plunger, a barrel and an exit,
   b) a biasing means to apply force to the plunger thereby causing the plunger to move relative to the barrel,
   c) a sensing means to determine a position of the plunger relative to the barrel, said sensing means comprising a ferromagnetic cylinder attached to the plunger and a coil encircling said ferromagnetic cylinder such that movement of the plunger causes a change in a position of the ferromagnetic cylinder within the coil and thereby changes the inductance of the coil,
   d) a solenoid actuator to restrict flow of the fluid from the exit of the syringe, and
   e) a controller means to control the means to restrict flow based upon feedback from the sensing means.

2. The infusion pump of claim 1, where the biasing means comprises a spring.

3. The infusion pump of claim 2, where the spring is incorporated within the barrel of the syringe.

4. The infusion pump of claim 2, where controllable application of current to the coil controls the rate of movement of the plunger in the barrel.

5. The infusion pump of claim 1, where the solenoid actuator to restrict flow comprises an actuator that squeezes a compressible tube attached to the exit of the syringe.

6. The infusion pump of claim 1, where controllable application of current to the coil controls the rate of movement of the plunger in the barrel.

* * * * *